March 19, 1957 C. G. DUEHRSEN Plant Pat. 1,581
ROSE PLANT
Filed June 8, 1956
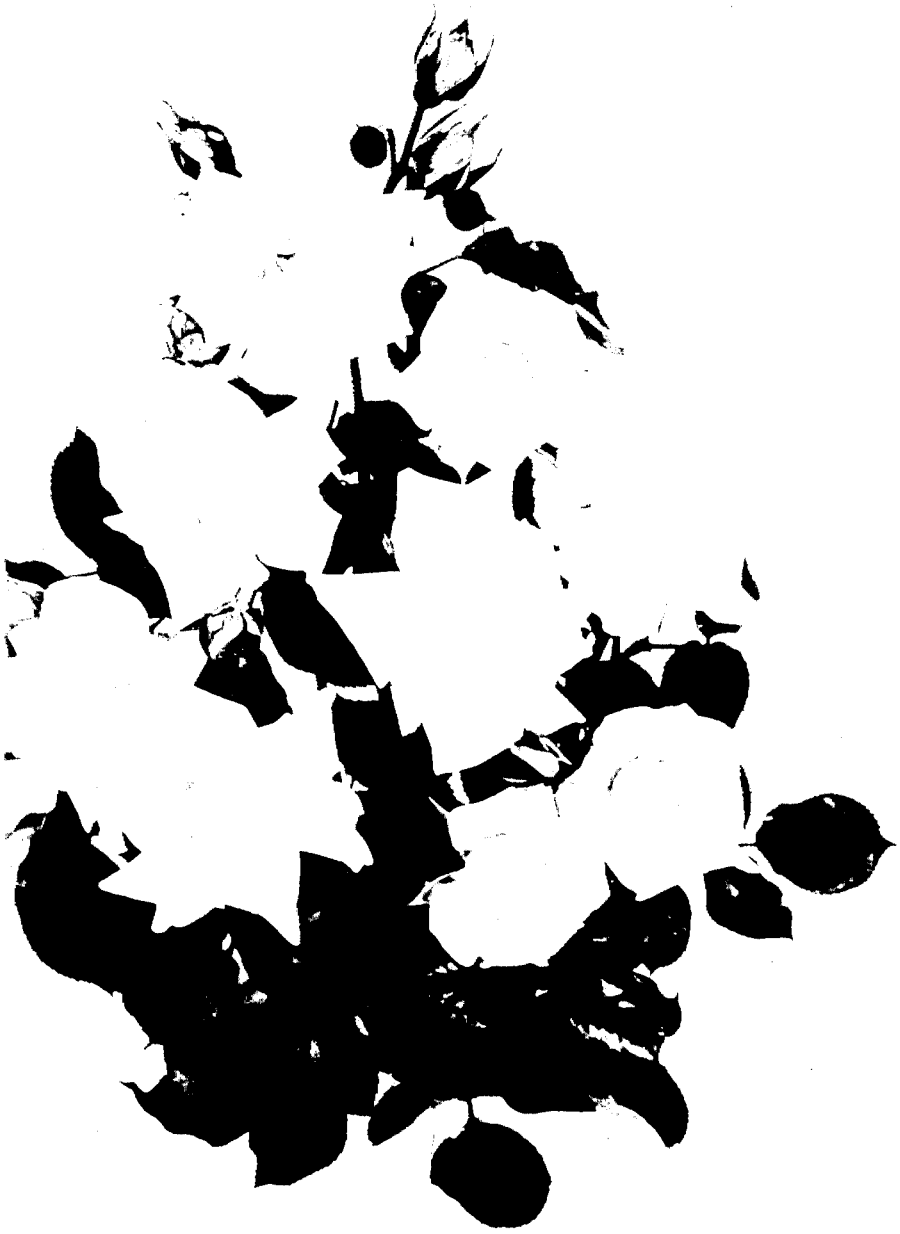
Inventor.
C. G. Duehrsen
By: Robb & Robb
Attorneys.

United States Patent Office

Plant Pat. 1,581
Patented Mar. 19, 1957

1,581

ROSE PLANT

Carl G. Duehrsen, Montebello, Calif., assignor to Constance A. Elmer, trading as Elmer Roses, San Gabriel, Calif.

Application June 8, 1956, Serial No. 590,337

1 Claim. (Cl. 47—61)

The present invention relates to a new and distinct variety of rose plant of the hybrid polyantha class, which was originated by me by crossing the variety "Captain Thomas" (Plant Patent No. 393) with an unnamed and unpatented seedling derived from "Baby Chateau" (unpatented) × "Fashion" (Plant Patent No. 789).

As the result of this breeding, I have produced a new rose variety which is definitely distinguished from its parents, as well as from all other varieties of its class, as evidenced by the following unique combination of characteristics which are outstanding in the new variety:

(1) The exceptionally good vigor of the plant and blooms;

(2) The distinctive color of the blooms; and (3) The good keeping qualities of both the color and the vigor of the blooms, even when cut from the plant.

Asexual reproduction of my new variety by budding, as performed by me at Montebello, California, shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Hardy; tall; bush; seedling; for cut flowers and for garden decoration.

Class: Hybrid polyantha.

Parentage: Seedling.

*Seed parent.*—"Captain Thomas."

*Pollen parent.*—An unnamed and unpatented seedling derived from "Baby Chateau" × "Fashion."

Propagation: Holds its distinguishing characteristics through succeeding propagations by budding.

*Flower*

Locality where grown and observed: Tulare, California.

Continuity: Continuous.

Fragrance: Moderate. Nature—spicy.

Flowers borne: Sometimes singly, and sometimes 2 or 3 to a stem; in irregular clusters; on long and strong stems.

Quantity of bloom: Abundant.

Bud:

*Peduncle.*—Short; heavy; stiff; medium smoothness. Color—Light bronze.

*Before calyx breaks.*—Size—medium. Form—short; without foliaceous appendages on the surface of the bud. Color—Primrose Yellow, Plate 601/3.

*As calyx breaks.*—Color—Primrose Yellow, Plate 601/2.

*As first petal opens.*—Size—small. Form—ovoid. Color: outside—Buttercup Yellow, Plate 5/2, blended with Fire Red, Plate 15/2, and Coral Pink, Plate 0619/1; inside—Buttercup Yellow, Plate 5/2, blended with Fire Red, Plate 15/2, Coral Pink, Plate 0619/1, Mars Orange, Plate 013/1, and Brick Red, Plate 016/1.

*Opening.*—Opens up well.

Bloom:

*Size (when fully open).*—Small; from 2½ to 3 inches.

*Petalage.*—Very double, with stamens not hidden; from 24 to 30 petals; arranged regularly.

*Form.*—Cupped-globular at first, but becoming cupped; petals being at first tightly rolled outward, but becoming cupped and rolled outward at maturity.

Petals:

*Texture.*—Thick; with both inside and outside satiny.

*Shape.*—Outside—oval; with apex having one notch. Intermediate—oval; with apex having one notch. Inside—oval; with apex having one notch.

This description of a newly opened flower was made from a rose grown outdoors in the month of May, at San Gabriel, California:

*Color.*—Outer petal: outside surface—Buttercup Yellow, Plate 5/2, blended with Fire Red, Plate 15/2 and Coral Pink, Plate 0619/1; inside surface—Buttercup Yellow, Plate 5/2, blended with Fire Red, Plate 15/2, Coral Pink, Plate 0619/1, Mars Orange, Plate 013/1 and Brick Red, Plate 016/1. Intermediate petal: outside surface—Buttercup Yellow, Plate 5/2, blended with Fire Red, Plate 15/2 and Coral Pink, Plate 0619/1; inside surface—Buttercup Yellow, Plate 5/2, blended with Fire Red, Plate 15/2, Coral Pink, Plate 0619/1, Mars Orange, Plate 013/1 and Brick Red, Plate 016/1. Inner petal: outside surface—Buttercup Yellow, Plate 5/2, blended with Fire Red, Plate 15/2 and Coral Pink, Plate 0619/1; inside surface—Buttercup Yellow, Plate 5/2, blended with Fire Red, Plate 15/2, Coral Pink, Plate 0619/1, Mars Orange, Plate 013/1 and Brick Red, Plate 016/1.

This description was made from a rose that was open for three days outdoors in the month of May, at San Gabriel, California:

*Color.*—Outer petal: outside surface—Buttercup Yellow, Plate 5/2, blended with Delft Rose, Plate 020/2; inside surface—Buttercup Yellow, Plate 5/2, blended with Delft Rose, Plate 020/3. Intermediate petal: outside surface—Buttercup Yellow, Plate 5/2, blended with Delft Rose, Plate 020/2; inside surface—Buttercup Yellow, Plate 5/2, blended with Delft Rose, Plate 020/3. Inner petal: outside surface—Buttercup Yellow, Plate 5/2, blended with Delft Rose, Plate 020/2; inside surface—Buttercup Yellow, Plate 5/2, blended with Delft Rose, Plate 020/3.

*General color effect.*—Newly opened flower— blend of yellow and red shades. Three-days open—blend of cream and light crimson shades.

*Behavior.*—Drop off cleanly; is not affected by cold, hot, wet or dry weather.

*Flower longevity.*—On bush in garden—5 days in April. Cut roses grown outdoors and kept at living room temperatures—5 days in April.

*Reproductive organs*

Stamens: Many; arranged regularly. Color—Buttercup Yellow, Plate 5/1.

Filaments: Medium length; many with anthers. Color—yellow.
Anthers: Medium size; all open at once. Color—yellow.
Pollen: Abundant. Color—lemon.
Pistils: Medium number.
Styles: Even; medium length; heavy; bunched.
Stigma: Color—white
Ovaries: All enclosed in calyx.
Hips: Globular; gourd-shaped; very smooth; walls fleshy. Color—green.
Sepals: Permanent; moderate length; recurved. Color—Garnet Brown, Plate 00918/3.
Seeds: Few; small.

*Plant*

Foliage:

*Leaves.*—Compound of 7 leaflets; abundant; medium size; glossy; wrinkled.

*Leaflets.*—Shape—oval, with acute apex. Base—round. Margin—serrate.

*Color.*—Mature: upper surface—dark green; under surface—light green. Young: upper surface—light green; under surface—very light green.

*Rachis (the supporting stem of the compound leaf).*—Medium caliper. Upper side—smooth. Under side—extremely smooth.

*Stipules.*—Medium length; narrow; with points turning out at an angle of less than 45°.

*Disease resistance.*—Resistent to mildew and blacksport, as determined by comparison with other varieties grown under comparable cultural conditions at San Gabriel, Montebello, and Tulare, California.

Growth:

*Habit.*—Bushy; upright.

*Growth.*—Vigorous.

*Canes.*—Medium caliper.

*Main stems.*—Color—brown. Thorns—few; straight; with broad base. Prickles—none. Hairs—none.

*Branches.*—Color—bright bronze. Thorns—few; medium length; straight; with broad base. Prickles—none. Hairs—none.

*New shoots.*—Color—bright bronze. Thorns—few; medium length; with broad base. Prickles—none. Hairs—none.

I claim:

A new and distinct variety of rose plant of the hybrid polyantha class, substantially as herein shown and described, characterized particularly as to novelty by the exceptionally good vigor of the plant and the blooms, the distinctive color of its blooms, and the good keeping qualities of both the color and the vigor of the blooms even when cut from the plant.

No references cited.